(12) United States Patent
Mayr et al.

(10) Patent No.: US 8,546,089 B2
(45) Date of Patent: Oct. 1, 2013

(54) CMYBP-C AND MLC2 AS DIAGNOSTIC MARKERS OF CARDIAC INJURY

(75) Inventors: Manuel Mayr, London (GB); Sebastien Jacquet, Saint-Jean-d'Arvey (FR); Michael Marber, London (GB); Mathias Gautel, London (GB)

(73) Assignee: King's College London, London (GB)

( * ) Notice: Subject to any disclaimer, the term of this patent is extended or adjusted under 35 U.S.C. 154(b) by 49 days.

(21) Appl. No.: 13/319,484

(22) PCT Filed: May 11, 2010

(86) PCT No.: PCT/GB2010/000935
§ 371 (c)(1),
(2), (4) Date: Mar. 7, 2012

(87) PCT Pub. No.: WO2010/130985
PCT Pub. Date: Nov. 18, 2010

(65) Prior Publication Data
US 2012/0156702 A1 Jun. 21, 2012

(30) Foreign Application Priority Data
May 11, 2009 (GB) .................................. 0908071.4

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 422/430

(58) Field of Classification Search
None
See application file for complete search history.

(56) References Cited

U.S. PATENT DOCUMENTS

| 5,604,105 A | 2/1997 | Jackowski |
|---|---|---|
| 2006/0257946 A1 | 11/2006 | Ding et al. |
| 2007/0207473 A1 | 9/2007 | Ackerman et al. |
| 2008/0300797 A1 | 12/2008 | Tabibiazar et al. |

FOREIGN PATENT DOCUMENTS

| WO | WO 90/15329 A1 | 12/1990 |
|---|---|---|
| WO | WO 2006/120391 A1 | 11/2006 |
| WO | WO 2008/104289 A1 | 9/2008 |

OTHER PUBLICATIONS

De Celle, Tijl et al., "Alterations in mouse cardiac proteome after in vivo myocardial infarction: permanent ischaemia versus ischaemia-reperfusion" Experimental Physiology, Jul. 2005, pp. 593-606, vol. 90, No. 4.
Katus, Hugo A. et al., "Diagnosis of Acute Myocardial Infarction by Detection of Circulating Cardiac Myosin Light Chains" American Journal of Cardiology, Nov. 1984, pp. 964-970, vol. 54.
Nagai, Ryozo et al., "Radioimmunoassay of Cardiac Myosin Light Chain II in the Serum Following Experimental Myocardial Infarction" Advances in Myocardiology, 1980, pp. 415-420, vol. 2.
Pinet, Florence et al., "Predicting left ventricular remodeling after a first myocardial infarction by plasma proteome analysis" Proteomics, May 2008, pp. 1798-1808, vol. 8, No. 9.
Sadayappan, Sakthivel et al., "Cardiac myosin binding protein c phosphorylation is cardioprotective" PNAS, Nov. 2006, pp. 16918-16923, vol. 103, No. 45.
Sadayappan, Sakthivel et al., "Cardiac Myosin Binding Protein-C Phosphorylation in a β-Myosin Heavy Chain Background" Circulation, Mar. 2009, pp. 1253-1262, vol. 119, No. 9.
Van Dijk, Sabine J. et al., "Cardiac Myosin-Binding Protein C Mutations and Hypertrophic Cardiomyopathy" Circulation, Mar. 2009, pp. 1473-1483, vol. 119, No. 11.
International Search Report for PCT/GB2010/000935 dated Oct. 14, 2010.
Search Report for GB0908071.4 dated Sep. 10, 2009.

*Primary Examiner* — Lisa Cook
(74) *Attorney, Agent, or Firm* — Knobbe Martens Olson & Bear LLP

(57) ABSTRACT

The invention relates to markers for acute myocardial infarction (AMI), particularly markers that may be used in the rapid and accurate diagnosis of AMI or reinfarction. A method of diagnosing cardiac injury comprising identifying an elevated concentration of cardiac myosin binding protein C (cMyBP-C) or a fragment thereof or myosin regulatory light chain 2 (MLC2) or a fragment thereof in a sample obtained from a subject.

12 Claims, 11 Drawing Sheets

US 8,546,089 B2

CMYBP-C AND MLC2 AS DIAGNOSTIC MARKERS OF CARDIAC INJURY

CROSS REFERENCE TO RELATED APPLICATIONS

This application claims the benefit and priority to and is a U.S. National Phase Application of PCT International Application Number PCT/GB2010/000935, filed on May 11, 2010, designating the United States of America and published in the English language, which is an International Application of and claims the benefit of priority to British Patent Application No. GB 0908071.4, filed on May 11, 2009. The disclosures of the above-referenced applications are hereby expressly incorporated by reference in their entireties.

FIELD OF THE INVENTION

The invention relates to markers for acute myocardial infarction (AMI), particularly markers that may be used in the rapid and accurate diagnosis of AMI or reinfarction.

BACKGROUND TO THE INVENTION

Acute myocardial infarction (AMI) is a common cause of death for which effective treatments are available providing the condition is rapidly diagnosed. The modern diagnosis of AMI relies on the rise and fall of a specific serum biomarker accompanied by an appropriate circumstance such as chest pain or revascularization. In this accepted paradigm the diagnosis cannot be ruled in or ruled out without the definite presence or definite absence of a serum biomarker. The ideal biomarker of cardiac injury should be cardiac specific and released rapidly after myocardial injury in direct proportion to the extent of damage. Furthermore the biomarker should have a high sensitivity and specificity. (1) Several biomarkers of AMI have been described in the literature but only a few have found their way into routine clinical practice of which none are ideal. For example, CK-MB starts to increase 4 to 8 hours after coronary artery occlusion and returns to baseline within 2-3 days. (2) However its use is limited by its presence in skeletal muscle and normal serum and by sensitivity of the assay to interference causing some to question its utility. (3) Myoglobin is another cytoplasmic protein found in cardiac and skeletal, but not smooth muscle. It is released even earlier, within 1-2 hours of AMI and peaks within 5 to 6 hours. (2) Unfortunately, any injury to skeletal muscle also causes elevated levels of myoglobin reducing specificity. Fatty acid binding proteins (FABP) are small (15 kDa) cytoplasmic proteins expressed in all tissues with active fatty acid metabolism. Amongst the nine proteins, heart-specific FABP (H-FABP) is found in heart, but also kidney, brain, skeletal muscle and placenta. (4) Following acute MI H-FABP can be detected within 20 minutes and peaks at 4 hrs considerably faster even than CK/CK-MB in the same patient cohort. Although H-FABP concentrations in normal plasma are low they are known to rise non-specifically during physical exertion (without a troponin rise), kidney injury and stroke. (5)

The most specific and sensitive cardiac proteins released after acute myocardial infarction are cardiac troponin I and T. Both troponin I and T are released slowly, peaking approximately 18 hours after MI, and remain elevated for 7 to 10 days. (2) This slow release is likely the result of their relatively inaccessible cellular location compared to CK-MB, myoglobin and H-FABP. Troponins regulate the physical interaction of actin and myosin and thus are found almost entirely associated within the crystalline structure of the sarcomere of striated muscle cells. (6) The troponin complex is composed of 3 forms: I, T and C. Troponins I and T exist as cardiac specific isoforms with epitopes that differ from the corresponding skeletal isoforms. In addition, the absent, or extremely low, normal circulating levels of troponin provides the greatest dynamic range of any of the currently available biomarkers. (7) Whilst there is no doubt troponins have revolutionized the detection and management of patients with AMI (8) they do have disadvantages. The slow release of troponin delays diagnosis and the initiation of specific treatments that could salvage heart tissue in those in whom it is raised. Similarly, patients in whom it is absent, and who are ultimately reassured and discharged, are admitted to hospital unnecessarily. Furthermore, the persistence of troponins limits their utility in the diagnosis of reinfarction. It is therefore widely accepted that there is a need for new biomarkers that can diagnose AMI earlier during its natural history and/or that have a short plasma half-life allowing use in diagnosis and quantification of reinfarction. The purpose of this study was to use the platform of the crystalloid perfused mouse hearts to perform a systematic proteomicanalysis of the coronary effluent after minimal AMI in order to identify new potential biomarkers.

SUMMARY OF THE INVENTION

According to the invention, there is provided a method of diagnosing cardiac injury, especially acute myocardial infarction (AMI) comprising identifying an elevated concentration of cardiac myosin binding protein C (cMyBP-C) or a fragment thereof or myosin regulatory light chain 2 (MLC2) or a fragment thereof in a sample obtained from a subject.

The method of the invention may be used to diagnose AMI or other cardiac injuries such as heart failure, myocarditis, pulmonary embolism and sepsis. Preferably the method is used to diagnose AMI.

The term AMI is well known in the heart and occurs when the blood supply to part of the heart is interrupted.

cMyBP-C is a well known protein. The sequence of the protein can be found at the uniprot database (http://www.uniprot.org/uniprot/) with the accession number Q14896 or MYPC3_HUMAN.

The sample preferably contains cMyBP-C or a fragment thereof. The fragment is preferably from the N terminal of the protein. The fragment preferably has a mass lower than 50 kDa, more preferably lower than 45 kDa, most preferably around 40 kDa. The fragment preferably comprises an amino acid sequence having substantial homology to the sequence of amino acids 1 to 362 of cMyBP-C. Substantial homology preferably means a homology of at least 75%, more preferably at least 80%, more preferably at least 85%, more preferably at least 90%. Most preferably the fragment comprises an amino acid sequence having the sequence of amino acids 1 to 362 of cMyBP-C.

MLC2 is a well known protein. The sequence of the protein can be found at the uniprot database (http://www.uniprot.org/uniprot) with the accession number P10916 (MLRV_HUMAN).

The sample is preferably a blood sample obtained from the patient. The sample may be venous or arterial blood, but is preferably peripheral venous blood. The sample is preferably a sample that has been obtained within 36 hours of the onset of symptoms of cardiac injury, especially pain, more preferably within 24 hours, even more preferably within 12 hours, most preferably within 6 hours of the onset of symptoms.

The term elevated concentration preferably means that the marker in question is present at a higher concentration in the sample than would be expected to be found in a sample from a subject not having suffered a myocardial infarction or than in a sample previously obtained from that individual. Expected levels may be predicted by sampling blood from a number of individuals and identifying a standard range of concentrations of cMyBP-C or MLC2 or fragments thereof.

When the marker is cMyBP-C, the concentration of cMyBP-C may be elevated, or the concentration of a fragment of cMyBP-C may be elevated. The concentrations may be elevated compared to standard predicted concentrations, or the concentration of fragment in relation to entire protein may be elevated. For example, the concentrations of the entire protein and the fragment may be compared and a change in expected ratio be used to indicate AMI.

When the marker is cMyBP-C, the concentration of cMyBP-C required to diagnose a patient as having suffered an infarction is preferably at least the standard concentration of cMyBP-C, more preferably at least five times the standard concentration, even more preferably at least ten times the standard concentration, most preferably at least fifteen, especially around nineteen times the standard concentration.

When the marker is MLC2, the concentration of MLC2 may be elevated, or the concentration of a fragment of MLC2 may be elevated. The concentrations may be elevated compared to standard predicted concentrations, or the concentration of fragment in relation to entire protein may be elevated. Again, the ratio of the protein to fragment may be identified and a change in ratio be used to indicate AMI.

The markers may be identified using any appropriate method, such as a binding assay, for example ELISA. Other methods, such as using high-performance liquid chromatography and mass spectrometric detection are also envisaged.

Also provided by the invention is the use of cMyBP-C or MLC2 as a marker of AMI.

Further provided is a kit for diagnosing AMI, comprising at least two of the following: a labeled binding molecule that binds specifically to cMyBP-C; a labeled binding molecule that binds specifically to a fragment of cMyBP-C; a labeled binding molecule that binds specifically to MLC2; and a labeled binding molecule that binds specifically to a fragment of MLC2.

Preferably the kit comprises a labeled binding molecule that binds specifically to cMyBP-C and a labeled binding molecule that binds specifically to a fragment of cMyBP-C.

A labeled binding molecule is any molecule that binds to the marker in question and which has a label to allow binding to be confirmed. Examples include labeled antibodies, such as ELISA (Enzyme-Linked Immunosorbent Assay) test labeled antibodies.

The invention will now be described in detail by way of example only with reference to the drawings.

A; Relationship between extent of infarction and duration of ischemia. Isolated retrogradely-perfused mouse hearts were subjected to 0, 5, 20 or 30 min of global ischemia (no flow) followed by 2 h reperfusion. Infarct size was demarcated by TTC staining.

B; Coronary effluent analysis by immunoblotting. Coronary effluents were collected after the indicated duration of global ischemia and probed for the CK-MB, troponin I and troponin T.

C; Samples were probed for the presence of IgG after 30 mins or 5 mins of perfusion (wash out).

D; Estimation of coronary effluent protein content by silver staining. Coronary effluents collected at the onset of reperfusion after the indicated period of ischemia were concentrated and analysed by 1D gel (5-20%) and silver stained. All bands were excised and, after in gel tryptic digestion, peptides were identified by MS-MS (proteins listed in supplementary table 1).

Figure 2:
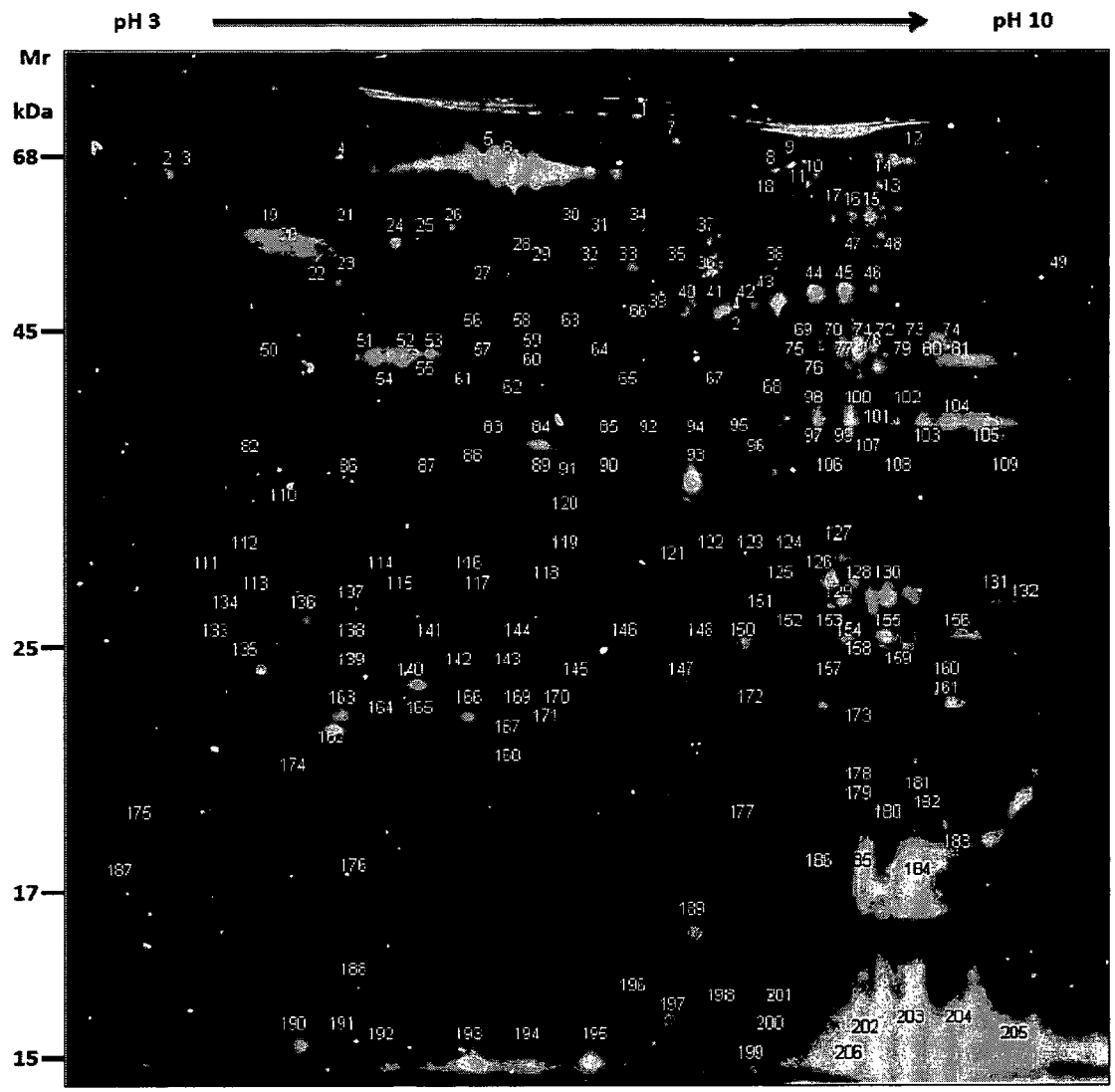

FIG. 2. A representative DIGE-2D gel of proteins appearing in coronary effluents after 5 min of global ischemia (Cy5, Red) and matched control perfusion (Cy3, Green). Coronary effluents from control and ischemic hearts have been concentrated and the same amount of protein has been Cy-dye labelled before separation by 2D gel electrophoresis. The annotated spots were excised and identified by LC-MS/MS. (See supplementary table 2 for the complete list of proteins).

Figure 3:
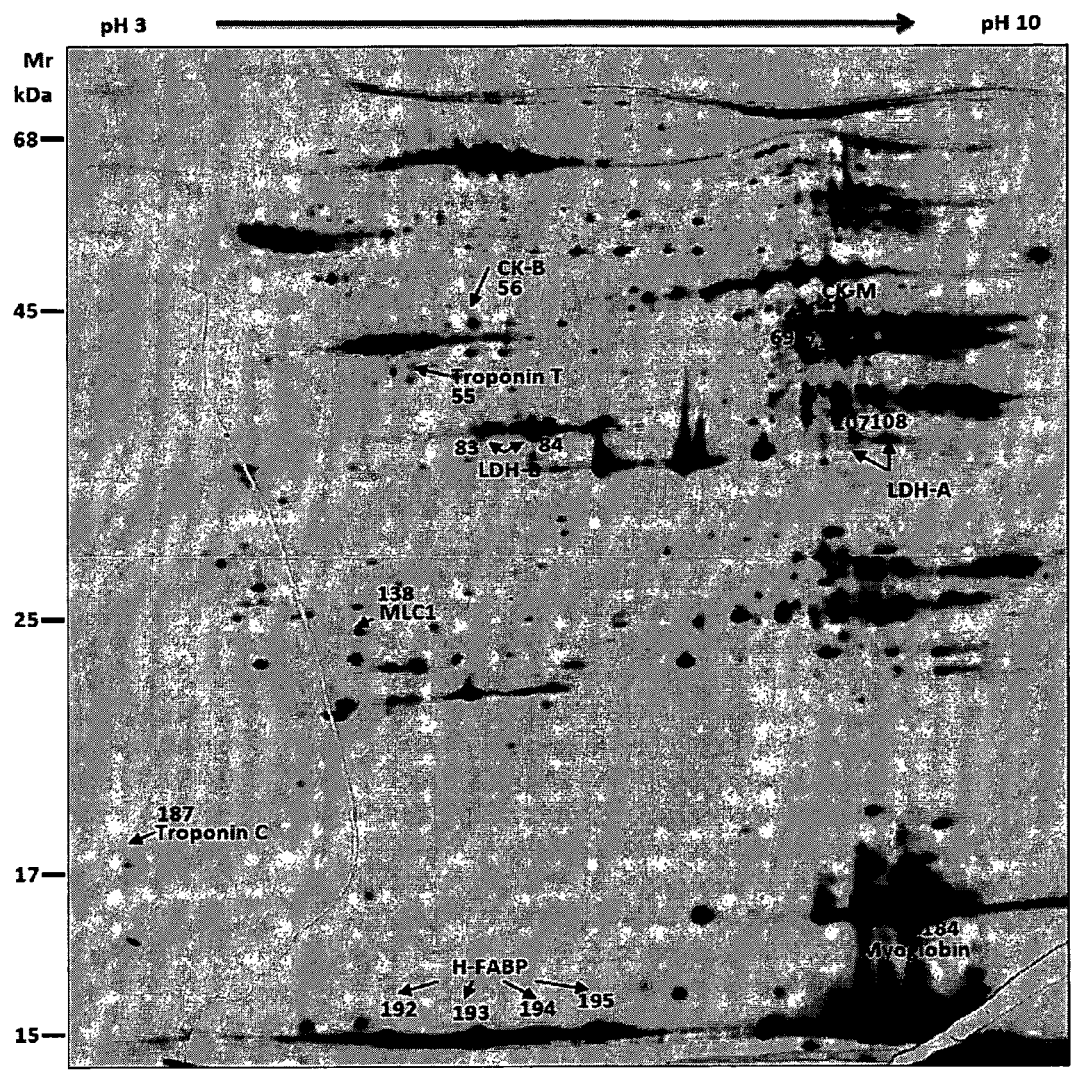

FIG. 3. A representative silver stained DIGE-2D gel of proteins appearing in coronary effluents after 5 min of global ischemia and matched control perfusion. The known biomarkers identified by mass spectrometry after harvest are indicated.

Figure 4:
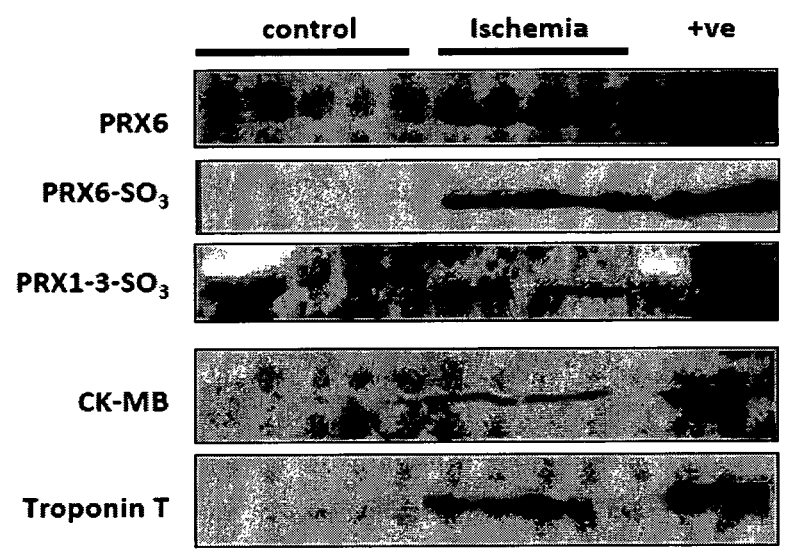
Figure 4:
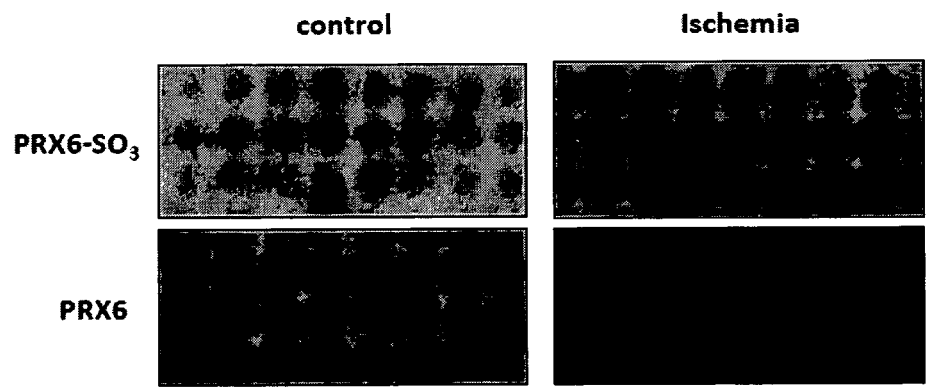

FIG. 4. Verification by immunoblotting of oxidative stress-related proteins appearing in the coronary effluent after ischemia.

A; Analyses of coronary effluents collected after 5 min ischemia or matching control perfusion by 1D electrophoresis. Peroxiredoxins and their post-translationally modified oxidized forms (Prx-SO3) were detected only after ischemia. Immunoblots for CK and troponin were used as controls to indicate ischemia-selective protein release.

B; Analyses of coronary effluents collected after 5 min ischemia or matching control perfusion by 2D electrophoresis. Immunoblots of a 2D gel (18 cm strip pH4-7, gradient gel 12-20%) for peroxiredoxin 6 total and oxidised forms. Peroxiredoxin 6 is present only in ischemic coronary effluent and several post-translational modifications can be visualized, amongst them the oxidised state Prx-SO3.

Figure 5:
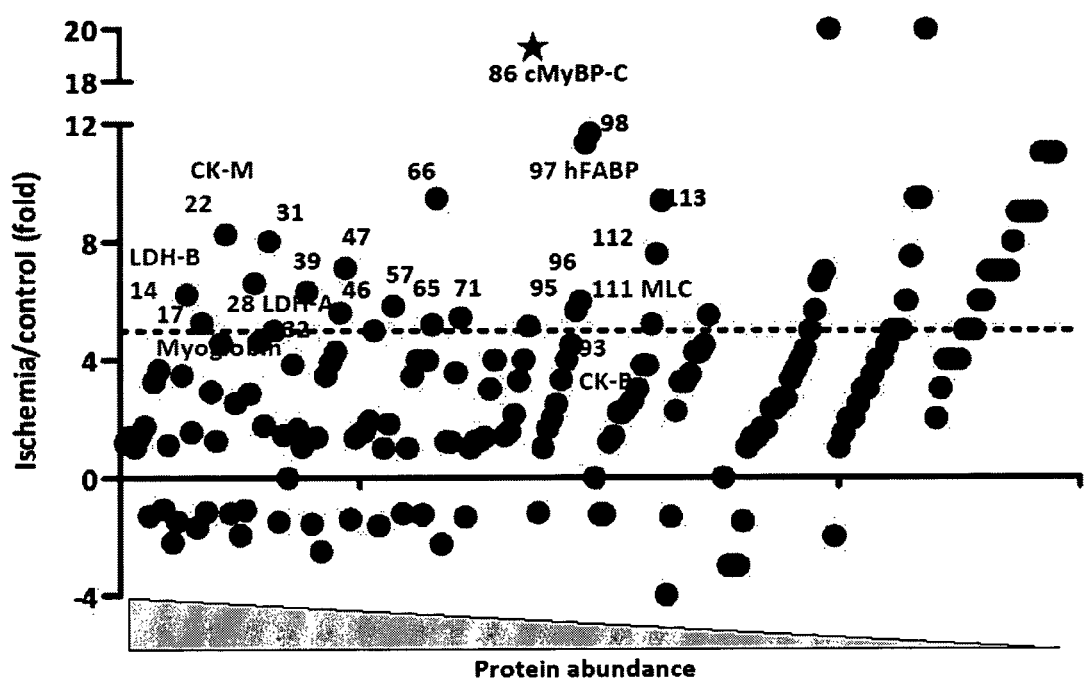

FIG. 5. Proteins released into the coronary effluent. Protein release after ischemia is plotted as fold change on the abscissa against absolute abundance on the ordinate. Abundance is estimated by the obtained spectral count normalized to the MW of the individual protein. The known biomarkers of myocardial infarction are highlighted in red and proteins in the coronary effluent that occupy a similar space on the plot are numerated and listed in table 4.

Figure 6:
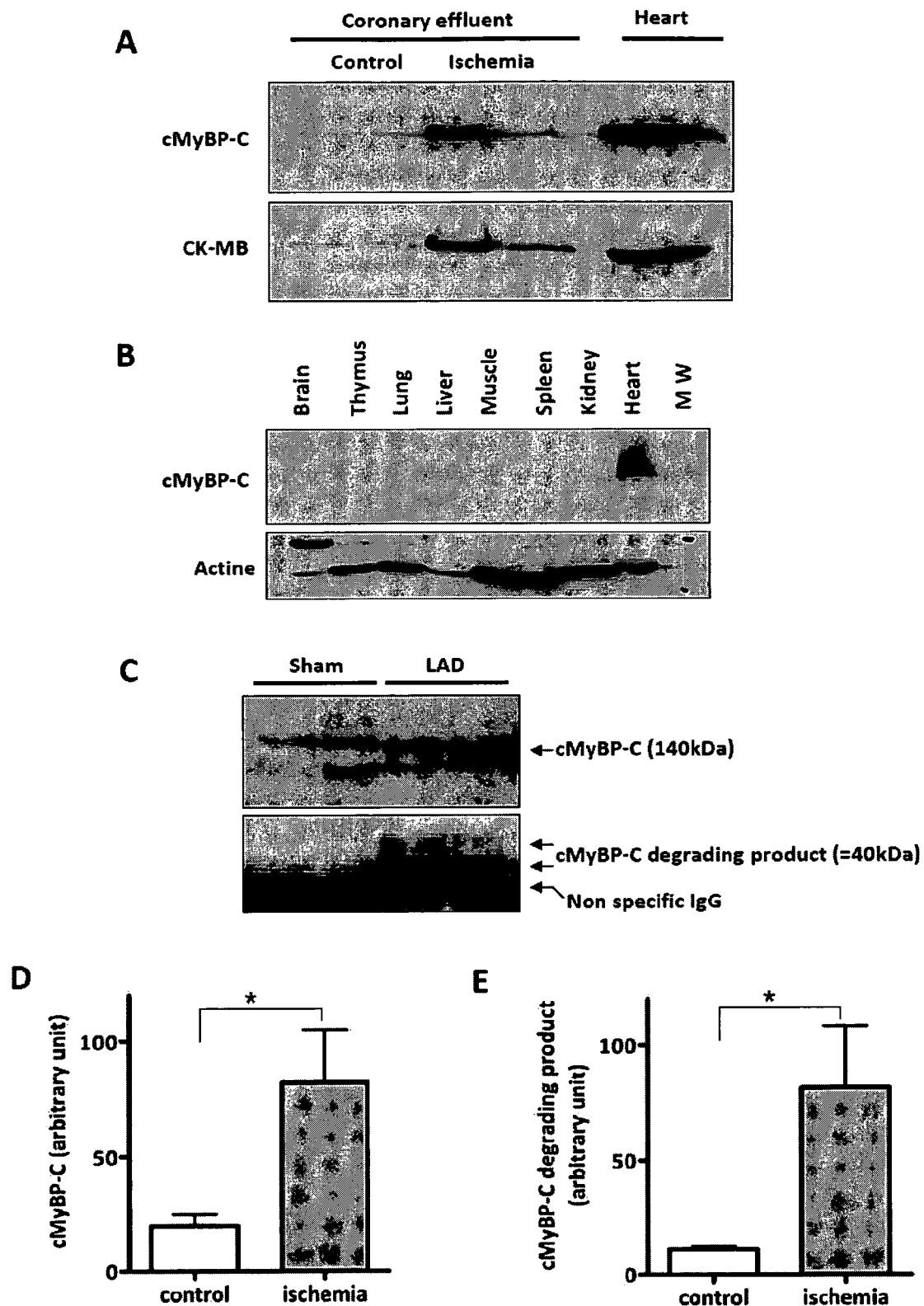

FIG. 6; Verification and validation of cMyBP-C as a potential new biomarker of acute myocardial infarction.

A; 1D separation and immunoblotting of proteins in coronary effluent. Coronary effluents were collected after 5 min ischemia or matching control perfusion.

B: cMyBP-C content amongst mouse organs. The anti-cMyBP-C antibody reacted only with cardiac tissue. Anti-actin was used as loading control.

C; Detection of cMyBP-C in the plasma of mice subjected to acute myocardial infarction. Mice were subjected to temporary ligation of the left anterior descending coronary artery (30 min) followed by reperfusion (2 hours). Blood was collected and plasma was immunoblotted for cMyBP-C. The full length cMyBP-c at 140 kDa, and the degradation product at 40 kDa, were both detected selectively in plasma of mice subjected to temporary, but not sham, coronary artery ligation.

D and E; Quantification of full length and short forms of cMyBP-C. Data are derived from N=6 mice per group.

Figure 7:
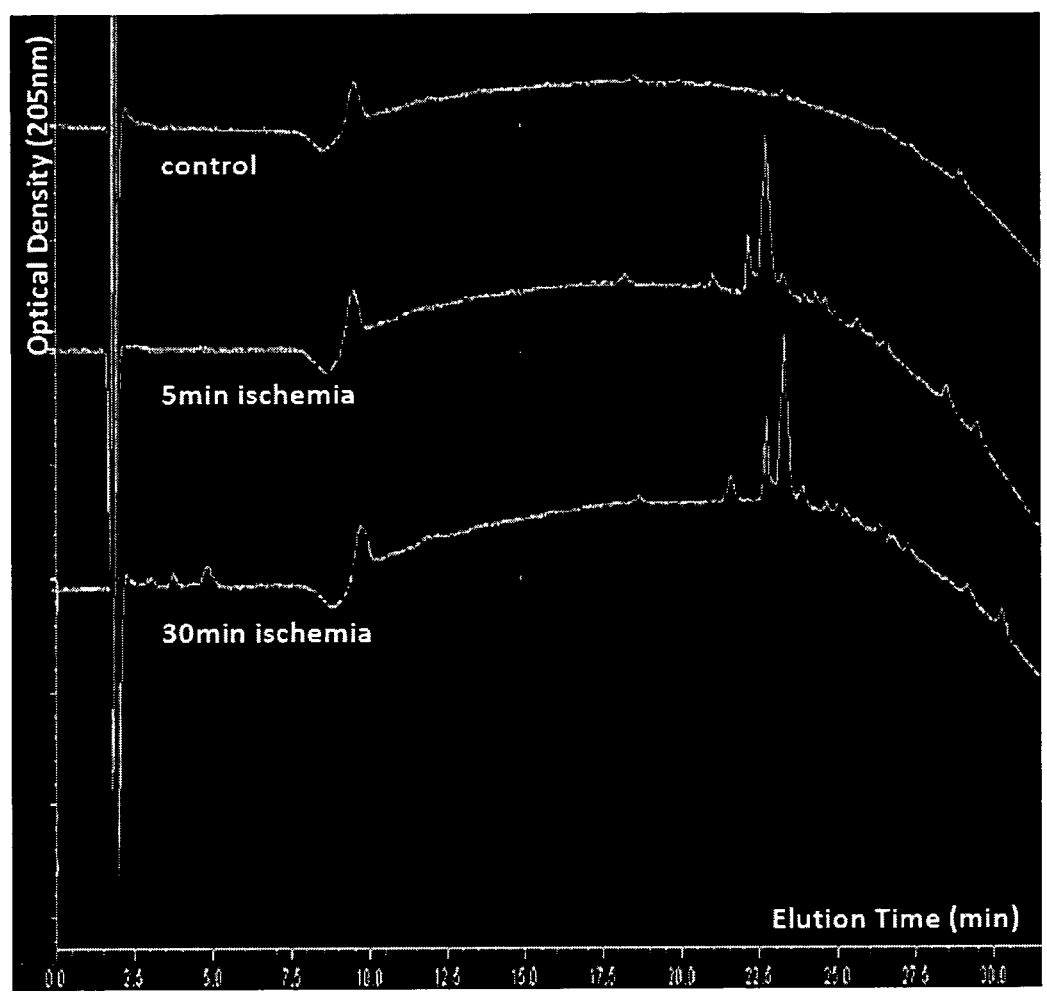

FIG. 7. Coronary effluents collected after the indicated period of ischemia and analysed by HPLC using a C8 zorbax column and detection at 205 nm and 280 nm Methods: Concentrated coronary effluent were directly analysed on reverse phase HPLC with a zorbax C8 column. Proteins were eluted using a gradient from 0% B to 100% B in 40 min at 1 ml/min where AB are a solvent system. Buffer A was composed of water added with 0.1% TFA, buffer B was composed of 10% water, 90% acetonitril and TFA 0.1%. Proteins and peptides were detected at 205 and 280 nm.

Figure 8:
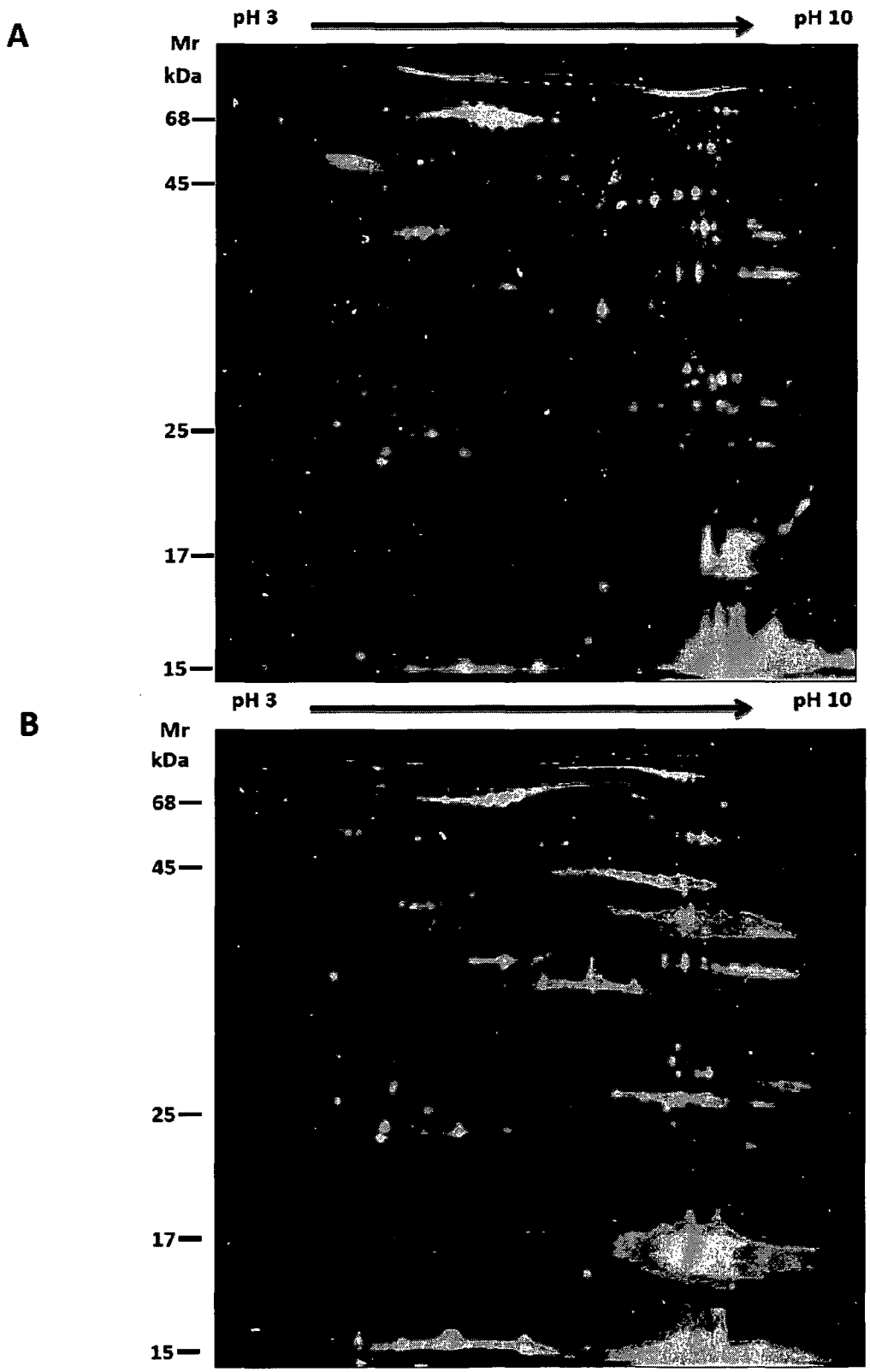

FIG. 8. Dye swap of 2D DIGE. Coronary effluents of control mouse hearts are labelled with Cy3 and of ischemic hearts with Cy5 (A). In panel B, the dyes are swapped between control and ischemic samples to exclude dye-specific artefacts.

Figure 9:
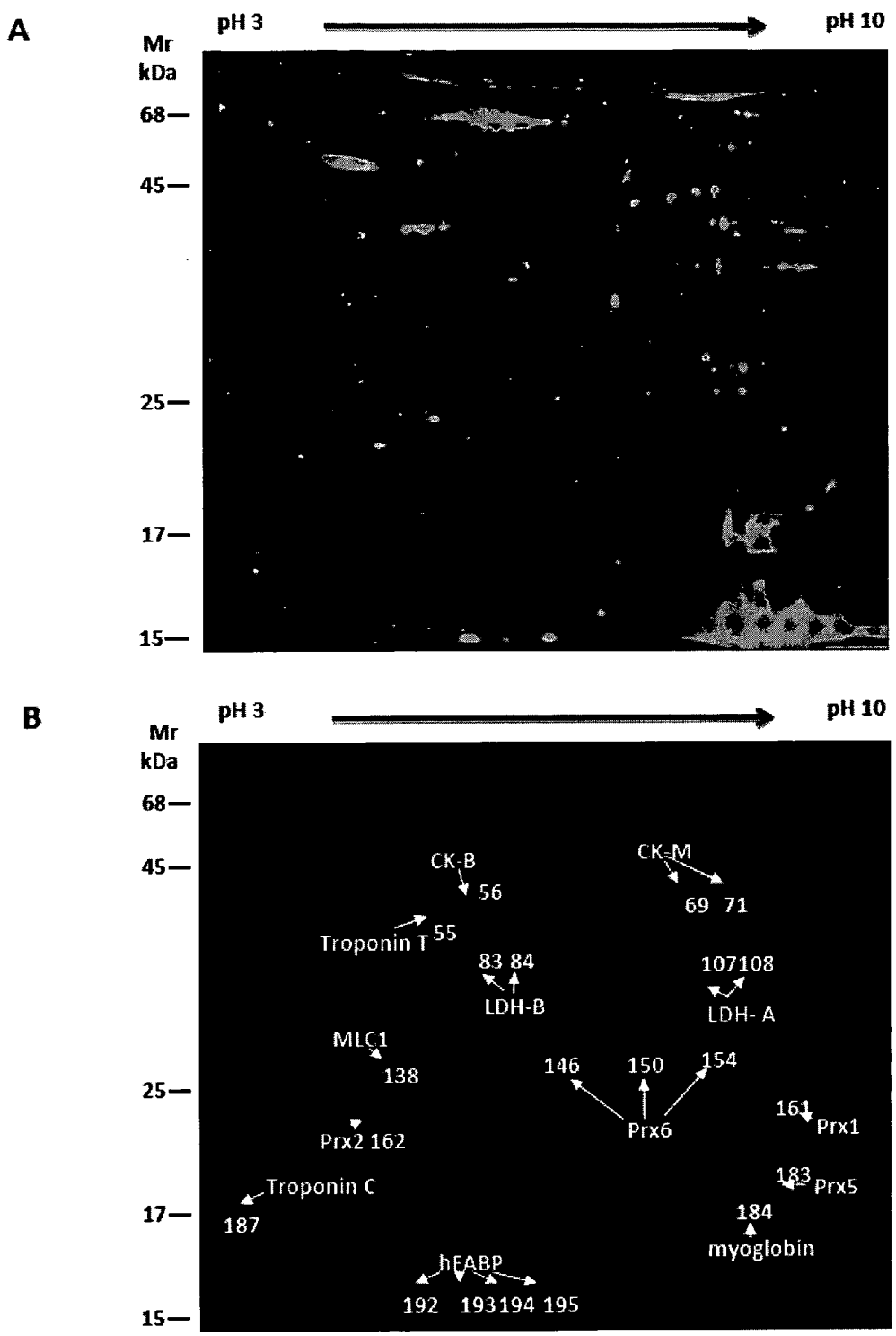

FIG. 9. A comparative view of DIGE fluorescence 2D gels. Coronary effluents of control mouse hearts are labelled with Cy3 (A, green colour) and of ischemic mouse hearts with Cy5 (B, red colour). Spots corresponding to known biomarkers of acute myocardial infarction and of proteins involved in the oxidative stress response are highlighted on the 2D gel (B).

Figure 10:
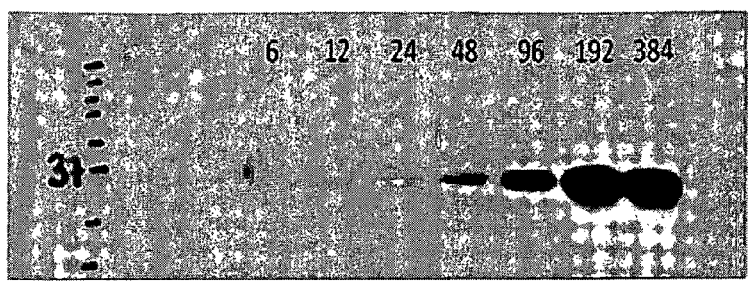

FIG. 10. cMyBP-C quantification

Increasing amounts of recombinant C0-C1 have been loaded (6 to 384 ng) in each well. The Primary antibody (A) was detected with a polyclonal anti-rabbit secondary. Although not clear on this reproduction a band is discernable at 6 ng on the original and with more prolonged exposure.

Figure 11:
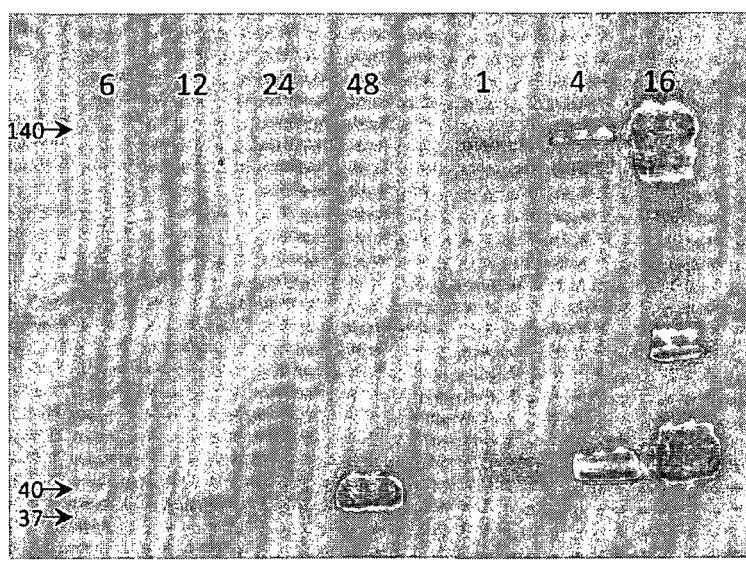

FIG. 11. Comparison of recombinant cMyBP-C with endogenous protein

The left-hand lanes comprise increasing amounts of recombinant C0-C1 protein (ng) and the right-hand lanes crude mouse heart stock homogenate (in μL). The primary antibody (A) detects cMyBP-C in its truncated and full length forms. The recombinant C0-C1 fragment runs at about 37 kDa whilst the dominant cleavage fragment of native cMyBP-C, present in crude heart homogenate, comprises 2 bands at approximately 40 kDa. Full length cMyBP-C runs at about 140 kDa. With 16 μL of crude homogenate a number of other degradation products are visible. All samples have been run on a single gel but intermediate lanes have been excised.

Figure 12:
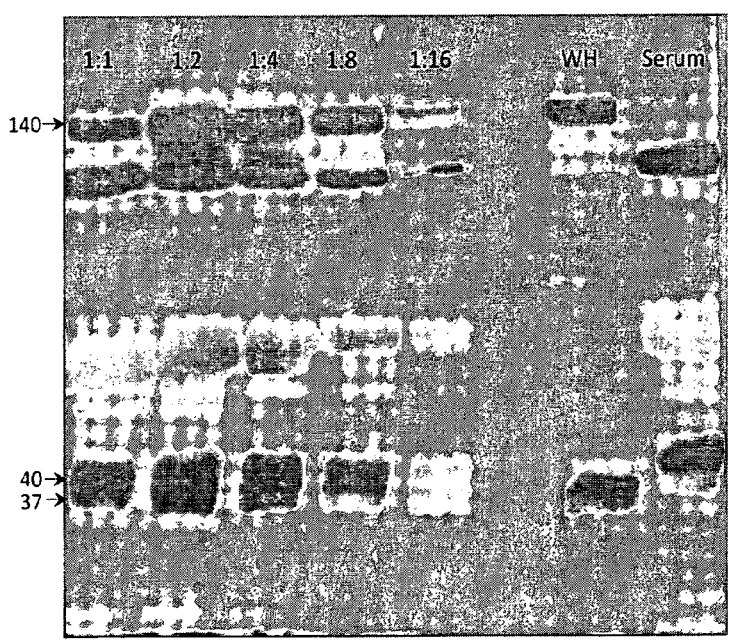

FIG. 12. Detection of myocardial-derived cMyBP-C in human serum

The right-hand lanes are human serum (serum) alone diluted 1:1 with sample buffer and 4 μL of whole heart stock homogenate (WH) as used in FIG. 2. The left-hand lanes are the stock homogenate (4 μL) made up to a volume of 30 μL with human serum diluted in increasing ratios of sample buffer from right (1:1) to left (1:16). The density of the band representing full-length MyBP-C (140 kDa) increases with moderately dilute serum (1:2 to 1:8) but is not present with serum alone. The second antibody binds non-specifically to a number of serum proteins, probably immunoglobulins, the most dominant of which runs just above 40 kDa interfering with the detection of the 40 kDa cMyBP-C fragment seen in WH lane. However, full length cMyBP-C runs above these non specific serum bands.

Figure 13:
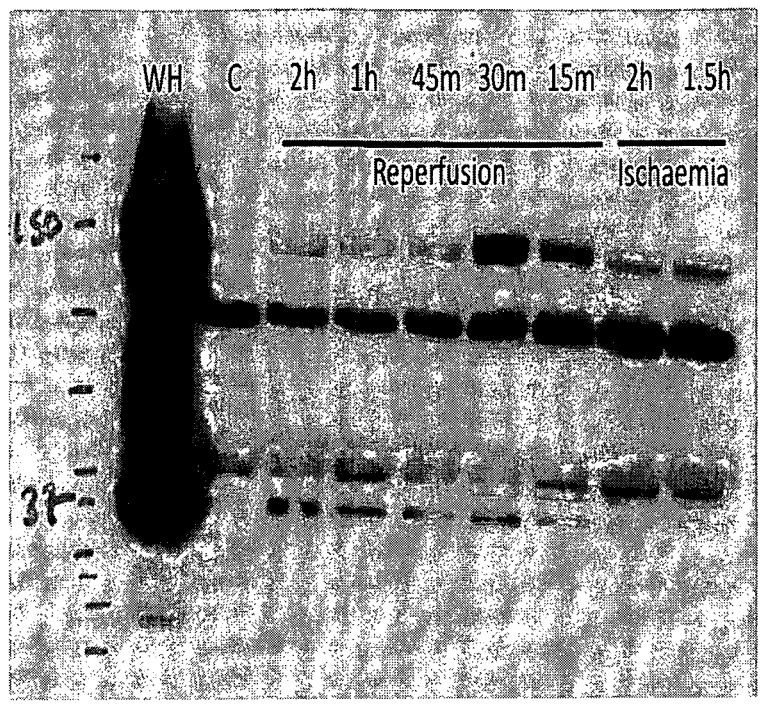

FIG. 13. Detection of full length cMyBP-C release in the serum of mice subjected to coronary artery ligation with and without reperfusion.

WH is whole mouse heart homogenate. Other samples are mouse serum diluted 1:1 with sample buffer. C is from a mouse without coronary artery ligation. Reperfusion samples are serum obtained from terminal bleeds of individual mice harvested at varied times after the release of a 30 minute coronary artery occlusion. Ischaemia samples are from terminal bleeds without release of the coronary artery occlusion which was maintained for 90 or 120 mins. Non-specific bands can be seen in C, however full-length cMyBP-C runs separately at 140 kDa. In addition a degradation fragment is also visible just below the immunoglobulin band at approximately 40 kDa. The full length fragment appears in the circulation very rapidly.

Figure 14:
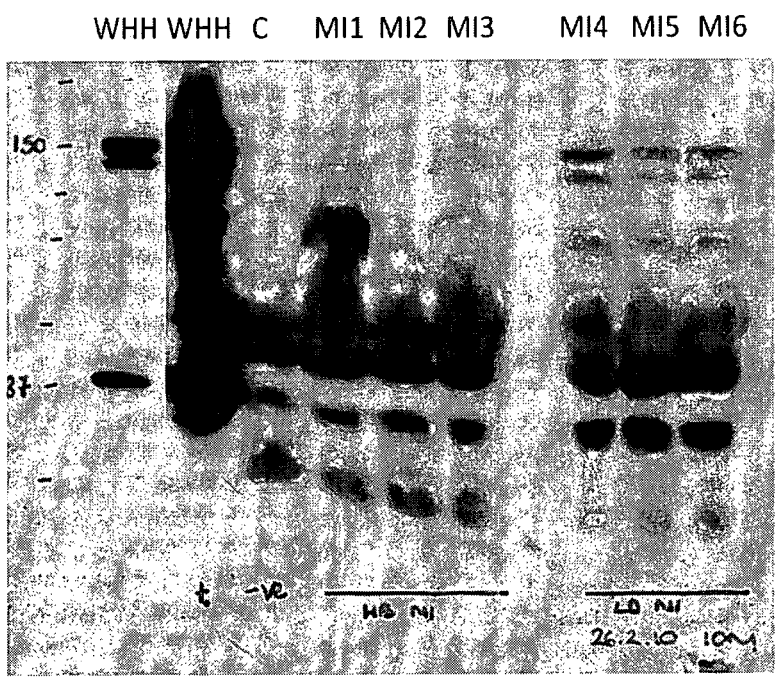

FIG. 14. Detection of full length cMyBP-C release in patients with AMI

Human serum from a volunteer (C) and patients with small (MI1-MI3) and large (MI4-MI6) AMIs diluted 1:1 in sample buffer. WHH is whole human heart homogenate. The left most lane is the same as the adjacent WHH lane but scanned from a shorter duration exposure of the membrane. The primary antibody (A) detects human cMyBP-C. Unfortunately the C1 lane has distorted and there may be a trace of spillover from the adjacent lane.

DETAILED DESCRIPTION OF THE INVENTION

EXAMPLE 1

Material and Methods:
Animals

All experiments were performed in accordance with United Kingdom Home Office *Guidance on the Operation of Animals* (*Scientific Procedures*) *Act* 1986, published by Her Majesty's Stationary Office, London and with the Guide for the Care and Use of Laboratory Animals published by the US National Institutes of Health (NIH Publication No. 85-23, revised 1996).

Perfusion of Isolated Murine Hearts

Male C57BL/6 mice were anesthetized with pentobarbital (300 mg/kg) and heparin (150 units) intraperitoneally. Hearts were rapidly isolated, mounted onto a Langendorff apparatus and retrogradely perfused at a constant pressure of 80 mmHg with Krebs-Henseleit buffer (in mmol/L: 118.5 NaCl, 25.0 NaHCO3, 4.75 KCl, 0.18 KH2PO4, 1.19 MgSO4, 11.0 D-glucose, and 1.41 CaCl2) equilibrated with 95% O2 and 5% CO2 at 37° C. Atrial pacing was performed at 580 bpm.

Experimental Protocol for Isolated Murine Myocardial Infarction Studies

A detailed method has been published previously. (9) Briefly, hearts were stabilized for 30 min after initiation of retrograde perfusion. All hearts underwent a period of global ischemia (as indicated in FIG. 1A) followed by 2 hours of reperfusion. At the end of reperfusion hearts were perfused with triphenyl tetrazolium chloride (TTC). Risk and infarct areas were calculated from surface area analysis of short axis slices of left ventricular myocardium. Infarct analysis, TTC-negative myocardium, was performed in all cases by an investigator blinded to the group assignments.

Experimental Protocol for Coronary Effluent Studies

Hearts were perfused on a Langendorff apparatus as previously described (9) with the following modifications: To limit non-ischemic damage to the heart, and thereby non-specific protein release, an intraventricular balloon was omitted. Hearts were stabilized for 30 minutes after initiation of retrograde perfusion to allow a complete wash-out of blood and limit the contamination of coronary effluent by plasma proteins. Hearts underwent 5 minutes of global ischemia (no flow) unless otherwise specified, and the coronary effluent was collected at the onset of reperfusion in a 5 mL aliquot with triton X100 at a final concentration of 0.05% to reduce the absorption of protein. (10) Aliquots were immediately frozen in liquid nitrogen.

Coronary effluents were thawed and kept at 4° C. at all times. Coronary effluent was concentrated using a Vivaspin column, with a cut-off of 3000 Da, from Sartorius.

Experimental Protocol for LAD Ligation In-Vivo

Coronary artery occlusion was achieved using the hanging weight system as previously described (11, 12). Mice were subjected to 30 minutes ischemia and 2 hours reperfusion and blood was taken by cardiac puncture at the end of reperfusion. Blood was centrifuged at 10000 g for 15 minutes at 4° C. and plasma aliquots were stored at −80° C.

Immunoblotting

Concentrated coronary effluents were separated by SDS-PAGE and immunoblotted using previously described protocols (9). The following primary antibodies were used against: creatine kinase M/B (#sc-28898 from Santa-Cruz), Troponin T (#ab10214 from Abeam), Troponin I (#4002 from Cell Signaling), Peroxiredoxin 6 (#LF-PA0011), peroxiredoxin 6-SO3 (#LF-PA0005), peroxiredoxin-SO3 (#LF-PA0004) all from Labfrontier. (#=catalogue number). Antibody directed against the C0-C1 region of cardiac myosin binding protein C was a gift from Prof Gautel M. (Randall institute, KCL, London). (13) For immunoblotting of 2D gels, concentrated coronary effluents from control or ischemic mouse hearts were pooled and concentrated further before using the "ready prep 2D clean-up" kit from Biorad following the manufacturer's instruction. 30 μg of protein extracts were loaded on an IPG strip (18 cm, pH4-7 non linear GE Healthcare) and then on a SDS-PAGE large gradient gel (12-20%) using a stacking gel.

1D gel-LC-MS/MS.

For proteomics, concentrated coronary effluents were reconstituted in Laemmli buffer and separated by SDS-PAGE gels. Large-format gradient gels (5-20%) were cast using the 2DE optimizer (NextGen Sciences, Huntingdon, UK). After the gels were overlaid with water-saturated butanol (2:1) and left to polymerise overnight, the stacking gel containing 4-5% acrylamide weakly buffered at pH 9.0 was cast over the already set resolving gel. Once samples were loaded, a constant 50 mA current was applied as proteins migrated down the stacking gel, at the stacking gel/running gel boundary the current was increased and maintained at 75 mA until the dye front reached the end of the gel. After silver-staining (Plus one silver staining kit, GE Healthcare), all gel bands were excised and subject to LC-MS/MS analysis.

Two-Dimensional Gel Electrophoresis.

Protein extracts prepared using the "ready prep 2D clean-up" were resuspended in lysis buffer (8M urea, 4% w/v CHAPS, 30 mM Tris-Cl, pH8.5) compatible with DIGE labeling (GE Healthcare). After centrifugation at 13,000 g for 10 min, the supernatant containing soluble proteins was harvested and the protein concentration determined using a modification of the method described by Bradford. The fluorescence dye labeling reaction was carried out at a dye/protein ratio of 400 pmol/100 μg. After incubation on ice for 30 min, the labeling reaction was stopped by scavenging non-bound dye with 10 mM lysine (L8662, Sigma) for 15 minutes. For two dimensional gel electrophoresis, samples were mixed with 2× buffer (8M urea, 4% w/v CHAPS, 2% w/v DTT, 2% v/v Pharmalytes 3-10 for IEF), 20 μg per sample were diluted in rehydration solution (8M urea, 0.5% w/v CHAPS, 0.2% w/v DTT, and 0.2% v/v Pharmalyte pH 3-10) and loaded on IPG strips (18 cm, pH 3-10, nonlinear, GE Healthcare). After rehydration overnight, strips were focused at 0.05 mA/IPG strips for 60 kVh at 20° C. (Multiphor II, GE Healthcare). Once IEF was complete the strips were equilibrated in 6M urea containing 30% v/v glycerol, 2% w/v SDS and 0.01% w/v Bromphenol blue, with addition of 1% w/v DTT for 15 min, followed by the same buffer without DTT, but with the addition of 4.8% w/v iodoacetamide for 15 min. SDS-PAGE was performed using 12% T (total acrylamide concentration), 2.6% C (degree of crosslinking) polyacrylamide gels without a stacking gel, using the Ettan DALT system (GE Healthcare). The second dimension was terminated when the Bromophenol blue dye front had migrated off the lower end of the gels. Fluorescence images were acquired using the Typhoon variable mode imager 9400 (GE Healthcare). Finally, gels were fixed overnight in methanol: acetic acid: water solution (4:1:5 v/v/v). Protein profiles were visualized by silver staining using the Plus one silver staining kit (GE Healthcare) with slight modifications to ensure compatibility with subsequent mass spectrometry analysis. For documentation, silver-stained gels were scanned in transmission scan mode using a calibrated scanner (GS-800, Bio-Rad). Match matrices were created by using Proteomeweaver 2.0 (Definiens). DIGE gels were analysed using the Decyder software (Version 6.5, GE healthcare). A detailed methodology is available on our website http://www.vascular-proteomics.com.

LC-MS/MS.

For tandem mass spectrometry (MS/MS), in-gel digestion with trypsin was performed according to published methods (14) modified for use with an Investigator ProGest (Genomic Solutions) robotic digestion system. 10 μL of sample was injected using an autosampler (Thermo Electron Corporation, CA) and loaded onto a 100×0.18 mm reverse-phase liquid chromatography (LC) column (BioBasic-18, particle size 5 μm, Thermo Electron Corporation) at 2 μl/min using a Surveyer MS pump (Thermo Electron Corporation, CA) and eluted with a 90 min gradient (0.1-30% B in 35 min, 30-50% B in 10 min and 50-80% B in 5 min where A=99.9% H2O, 0.1% formic acid and B=99.9% acetonitrile, 0.1% formic acid). The column was coupled to an electrospray source and spectra were collected from an ion-trap mass analyzer (LCQ Deca XP Plus, Thermo Electron Corporation) using full ion scan mode over the mass-to-charge (m/z) range 300-1800. MS/MS was performed on the top three ions in each MS scan using the data-dependent acquisition mode with dynamic exclusion enabled. MS/MS spectra were matched to database entries (UniProt Knowledgebase Release 7.5, consisting of: UniProtKB/Swiss-Prot Release 49.5 and UniProtKB/TrEMBL Release 32.5 of 18 Apr. 2006) using TurboSE-QUEST software (Bioworks 3.3, Thermo Finnigan). All peptide sequence assignments were required to result from fully tryptic cleavages of the corresponding proteins. Scaffold (version 1.0, Proteome Software Inc., Portland, Oreg.) was used to validate MS/MS based peptide and protein identifications. Peptide identifications were accepted if they could be established at greater than 95.0% probability as specified by the Peptide Prophet algorithm. Protein identifications were accepted if they could be established at greater than 99.0% probability and contained at least 2 identified peptides. Protein probabilities were assigned by the Protein Prophet algorithm.

Results

The Model of Langendorff-Perfused Murine Hearts.

Figure 1:
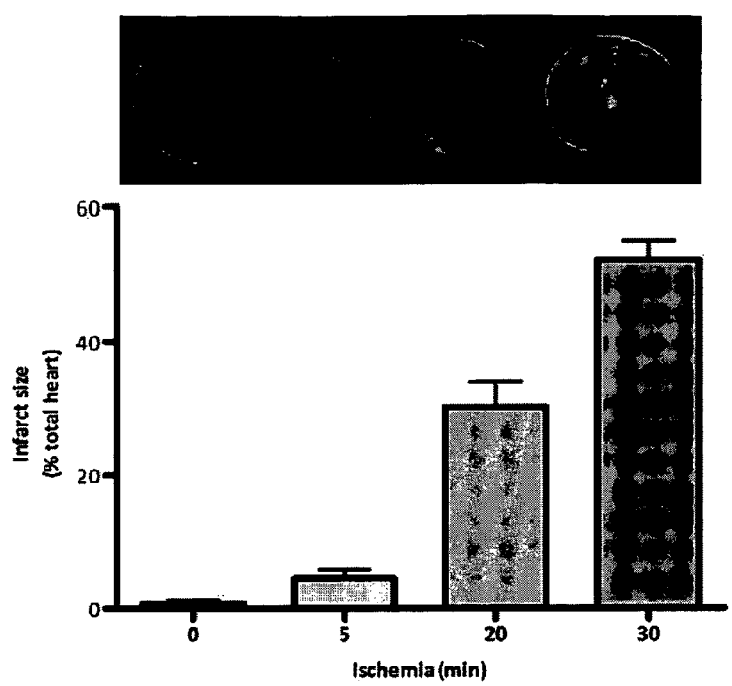
FIG. 1. Characterization of myocardial infarction and coronary effluent protein content.
Figure 1:
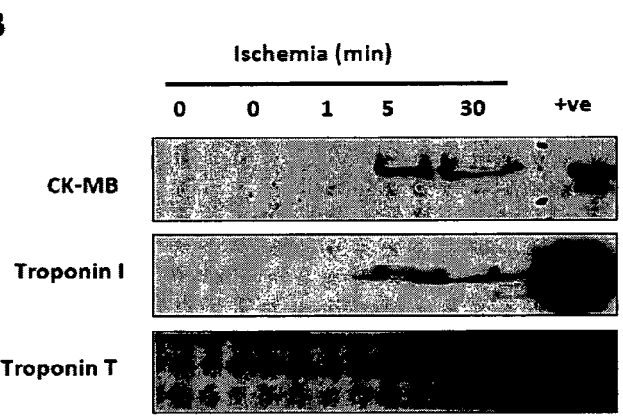
Figure 1:
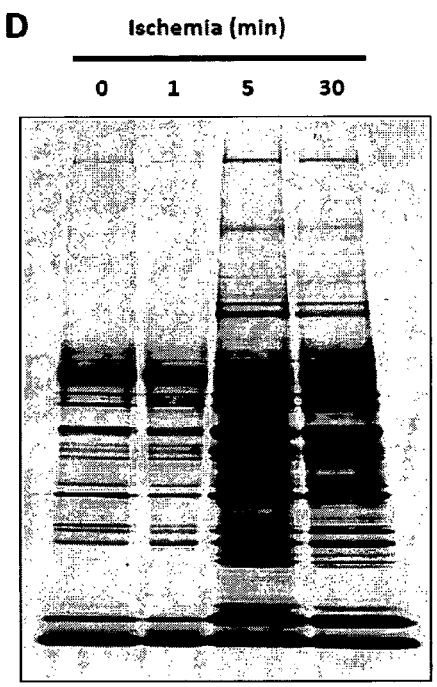
Figure 1:
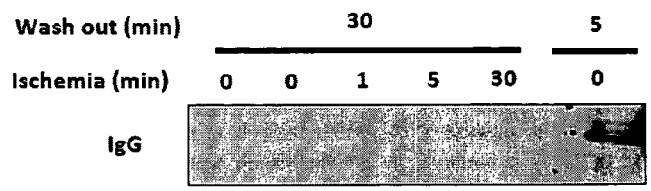

To mimic myocardial ischemia, we used Langendorff-perfused mouse hearts. In this model, the heart is retrogradely perfused with a standard protein-free buffer (Krebs Henseleit Buffer) at a constant pressure. Before the index ischemia, all hearts were perfused for 30 minutes to allow recovery of normal function (15) and to avoid a carry-over of plasma proteins. Compared to shorter stabilization/wash-out periods, there was significantly less IgG in the coronary effluent (FIG. 1C). The time-dependent effect of ischemia on infarct size is shown in FIG. 1A: the infarct size increased from 4.5% to 50% with 5 min to 30 minutes of global ischemia. The coronary effluent was collected after 1, 5 and 30 minutes of ischemia and examined for the release of known biomarkers of tissue damage by immunoblotting. FIG. 1B shows the release of creatine kinase (a cytoplasmic protein) and of troponin I and troponin T (myofilament proteins) after 1, 5 or 30 minutes duration of ischemia. It is important to note that these markers of myocardial injury are not present in the control hearts (0 minutes) confirming that cardiac excision and perfusion, in the absence of ischemia, does not cause discernable damage. We were unable to detect the release of markers of myocardial injury with the shortest duration of ischemia (1 minute) suggesting detectable injury occurs between 1 and 5 minutes in this model. The protein release profile in isolated perfused heart is greatly accelerated compared to that occurring in-vivo and a similar rapid release of CK has previously been described.(16, 17) This is likely the result of relative hyperperfusion caused by the low viscosity of the perfusate. The protein release in the coronary effluent was monitored by reversed phase HPLC (Supplementary FIG. 1). Consistent with a previous report by Van Eyk (17), we observed a predominant peak eluting around 23 min using a C8 Zobrax column. As expected, the protein release increased with the duration of ischemia.

Coronary Effluent Analysis by 1D gel-LC-MS/MS.

To reduce the complexity of the sample, the coronary effluents were first separated on large format gradient gels (5-20%) and stained with silver (FIG. 1D). Notably, the shortest ischemia duration at which there was a detectable difference in the coronary effluent compared to baseline protein release was at 5 min. Although this time point caused only minor infarction (see FIG. 1A) it was used for further proteomic analysis. All bands were excised from the gel, subject to tryptic digestion, and identified by nanoflow reverse phase chromatography tandem mass spectrometry. In total, 487 proteins were identified in the ischemic coronary effluent compared to only 209 in the control samples (see supplementary table 1 for complete list of proteins). Thus, 278 proteins were unique to ischemia reperfusion samples. Moreover, all known biomarkers of myocardial injury, such as troponins I, C, T, creatine kinase, lactate dehydrogenase, myoglobin, heart-specific fatty acid binding protein, aspartate aminotransferase etc. were among the proteins identified (table 1). Relative quantification of the protein release after ischemia was obtained by using the normalized spectral count. Whereas troponin I, troponin T, troponin C were only detected in the coronary effluent after ischemia, but not at baseline, other markers such as CK, FABP, LDH, etc were present under both conditions (table 1). However, the number of peptides identified for CK increased by 8-fold, FABP by 11 fold, and lactate dehydrogenase by 6 fold in ischemic compared to normoxic hearts and their appearance/enrichment underscores their potential as clinical biomarkers for myocardial injury.

Coronary Effluent Analysis by Difference-in Gel Electrophoresis (DIGE)

Post-translational modifications of albumin caused by oxidative stress during ischemia reperfusion, known as ischemia modified albumin (IMA), are already used clinically as a biomarker of ischemia. To determine whether similarly useful post-translational modifications occurred in proteins in the coronary effluent, control and ischemic samples were analyzed by difference in-gel electrophoresis (DIGE) 2D (FIG. 2). Results were reproduced by using a dye swap (Supplementary FIG. 2). The fluorescence intensity was quantified for more than 200 spots. After silver staining, all spots were excised and identified by tandem mass spectrometry. The list of proteins identified is presented in supplementary table 2. Quantitative values were obtained by using the Decyder software (GE Healthcare). The DIGE-approach confirmed the quantitation based on spectral counting in that known markers of cardiac infarction such as, troponin T, troponin C, CK MB isoforms, FABP, LDH and myoglobin were present in higher abundance in ischemic than control samples (table 2 and FIG. 3).

Verification by Immunoblotting of the Proteomic Identification of Oxidative Stress-Related Proteins.

Oxygen and other free radicals are generated in the ischemic and reperfused heart and are important mediators of post-ischemic injury (for review see (18)). Our proteomic analysis revealed the release of numerous proteins involved in neutralizing free radicals following ischemia/reperfusion, including thioredoxin reductase, peroxiredoxins, etc. (see table 3). In addition, the separation by 2D gel electrophoresis also revealed that ischemic injury induced an acidic shift in the isoelectric point of proteins containing redox-active cysteines as illustrated for Peroxiredoxin 6 (Supplementary FIG. 3B). This finding is consistent with previous reports confirming sulfoxidation as a common posttranslational modification in redox-sensitive proteins (19). To confirm the presence of these potentially cardioprotective proteins in ischemic coronary effluents, we validated our findings by immunoblotting. The release of peroxiredoxin 1-3 and 6 was not only significantly higher in ischemic compared to control samples (FIG. 4A), but antibodies against oxidized peroxiredoxin 6 also confirmed the presence of the oxidized isoform after myocardial ischemia by immunobloting on 1D gel (FIG. 4A) and on 2D gel (FIG. 4B). Thus, the proteomic analysis revealed evidence for posttranslational modifications of antioxidant-defense proteins in ischemic coronary effluents.

Myosin Binding Protein C as New Candidate Biomarker of Myocardial Injury.

In FIG. 5, proteins in the post-ischemic coronary effluent are plotted according to their estimated abundance based on the normalized spectral count. The fold change compared to control hearts is plotted on the y-axis. Most known biomarkers cluster at the top left depicting highly abundant proteins with a pronounced propensity to leak into the coronary effluent after ischemia. Interestingly, cardiac myosin binding protein C (cMyBP-C) appeared in a similar region (FIG. 5) and its fold change (19 fold) exceeded that of many established biomarkers. We subsequently verified the release of cMyBP-C in coronary effluent by immunoblotting (FIG. 6A) using an antibody directed against the C0-C1 region of cMyBP-C, which is only present in the cardiac isoform (FIG. 6B) (for review see (20)). We further confirmed ischemia-selective cMyBP-C release into plasma after regional myocardial ischemia and reperfusion in-vivo. Interestingly, we were not only able to detect a band at 140 kDa, corresponding to the full-length cMyBP-C, but also a degradation product at 40 kDa (FIG. 6C,D,E), which has previously been noted in post-ischemic myocardium (21, 22). Thus, our proteomic approach has validated a number of existing biomarkers and revealed a cardiac-specific potential new marker detectable with only minor myocardial injury.

Discussion

The aim of this study was to identify potential new biomarkers by comprehensively analyzing the proteins released into the coronary effluent after a duration of myocardial ischemia chosen to cause mild injury. Our extensive proteomic analysis confirmed the presence of all existing biomarkers of acute myocardial infarction (AMI) but also revealed posttranslational modifications of antioxidant proteins and identified the cardiac isoform of myosin binding protein C (cMyBP-C) as a potential novel biomarker. Furthermore, using an in-vivo murine model of AMI we could detect cMyBP-C in the plasma.

Langendorff-perfused mouse hearts formed the basis of our discovery platform. This model recapitulates true ischemic injury and allows a careful titration of the duration of ischaemia to cause minimal, but definite, AMI. Furthermore the model has the advantage of limiting contamination of the coronary effluent by plasma proteins. The choice of this model was vindicated by its ability to identify all the commonly used existing biomarkers of AMI (troponin I, troponin T, creatine kinase, FABP, LDH, myoglobin). An extensive proteomics analysis of the coronary effluent identified nearly 500 proteins using a 1D gel LC-MS/MS approach and around 200 proteins using the DIGE platform. The proteomics analysis revealed that the troponins, the current gold standard to assess AMI, are among the most abundant proteins in ischemic coronary effluents and show minimal leakage from normoxic myocardium (Table 1).

Over the last few years, proteomics has been used extensively for the discovery of potential biomarkers for cancer (23), atherosclerosis (24), and cardiovascular disease (for review see(25)). Plasma and serum were routinely used for biomarker discovery although the dynamic range of plasma proteins spans 9 orders of magnitude and just 5 proteins typically constitute more than 90% of the total protein mass. This complexity exceeds the analytical capabilities of most proteomic approaches. Despite these evident difficulties, several proteomic studies have been undertaken to discover predictive cardiovascular biomarkers, but most studies failed to detect the existing biomarkers and revealed only changes in high abundant plasma proteins (26). In an alternative approach, we analyzed the coronary effluent in an ex vivo model where the heart was perfused with a crystalloid buffer without proteins. This approach has previously been used by Koomen et al (27) in a model of ischemia/reperfusion injury in rat hearts, but they encountered a high contamination with plasma proteins (30% of the 342 proteins identified were of plasma origin), which minimizes the chance of detecting potential cardiac-specific biomarkers. By extending the washout period and perhaps by using smaller hearts, we managed to substantially reduce the contamination by plasma proteins. Moreover, we employed the latest ion trap technology (LTQ Orbitrap) and used a 1D gel-LC/MS/MS approach besides 2D gel electrophoresis. This allowed us to detect substantially more proteins, including all the standard biomarkers of myocardial injury, which contrasts with previous publications (27).

A methodological question arose during this study as to whether proteomic analysis should be done on the same volume of coronary effluent or on the same quantity of protein released. It is well established that during ischemia reperfusion there is an increased protein release by the myocardial tissue. To reflect this pathophysiological phenomenon, we compared the same volume of coronary effluents from control and ischemic hearts in the 1D gel-LC/MS-MS experiment. To identify ischemia-specific post-translational modifications, however, we compared the same quantity of proteins in the DIGE experiment. Although fewer proteins were detected in the 2D gel-based approach compared to the 1D gel-LC/MS/MS approach, it is noteworthy that the known biomarkers of cardiac injury were identified in both experimental approaches.

The identification of the cardiac isoform of myosin binding protein C in ischemic coronary effluents fulfilled some of the criteria of good biomarker candidate: namely a cardiac specific protein with a pronounced change in response to ischemic injury. Notably, the presence of cMyBP-C and a 40 kD degradation product was only found in the plasma of mice with AMI. The later fragment corresponds to the N-terminal part of cMyBP-C and was previously described in mouse hearts subjected to ischemia reperfusion (21) and in dog hearts subjected to low flow ischemia (22). However, its release into the circulation after myocardial injury has not been previously reported and it may provide physiological circumstance-specific information. The troponins have revolutionized the management of AMI. However, it is possible cMyBP-C is released more quickly and has a shorter circulating half-life. If this is the case it would have the advantage of allowing more rapid rule in, and rule out, of AMI in patients with chest pain. A further advantage is that it could allow the diagnosis and the quantification of re-infarction in patients in whom AMI is confirmed. This would be of particular advantage in trials of interventional devices that are thought to diminish periprocedural AMI.(28)

In summary, the present study aimed to identify potential new biomarkers of AMI. We performed a comprehensive identification of proteins released in coronary effluent during myocardial ischemia, which revealed the cardiac isoform of myosin binding protein C as a potential new biomarker. Further studies in humans will be necessary to corroborate these findings and assess the clinical advantage, if any, of cMyBP-C over existing biomarkers of AMI.

EXAMPLE 2

The inventors looked into the quantification of cMyBP-C further and also compared recombinant cMyBP-C with the endogenous protein. The results are shown in FIGS. 10 and 11. The inventors then went on the detect myocardial derived cMyBP-C in human serum. The results are shown in FIG. 12.

Full length cMyBP-C was detected in the serum of mice subjected to coronary artery ligation. A 40 kDa fragment could also be seen. Results are shown in FIG. 13. Further, the inventors were able to detect the release of full length cMyBP-C in patients with AMI.

References
1. Rajappa, M., and Sharma, A. (2005) Biomarkers of cardiac injury: an update. *Angiology* 56
2. Apple, F. S., Wu, A. H., Mair, J., Ravkilde, J., Panteghini, M., Tate, J., Pagani, F., Christenson, R. H., Mockel, M., Danne, O., and Jaffe, A. S. (2005) Future biomarkers for detection of ischemia and risk stratification in acute coronary syndrome. *Clin Chem* 51.
3. Saenger, A. K., and Jaffe, A. S. (2008) Requiem for a Heavyweight: The Demise of Creatine Kinase-MB. *Circulation* 118.
4. Pelsers, M. M., Hermens, W. T., and Glatz, J. F. (2005) Fatty acid-binding proteins as plasma markers of tissue injury. *Clin Chim Acta* 352.
5. Wunderlich, M. T., Hanhoff, T., Goertler, M., Spener, F., Glatz, J. F., Wallesch, C. W., and Pelsers, M. M. (2005) Release of brain-type and heart-type fatty acid-binding proteins in serum after acute ischaemic stroke. *J Neurol* 252.
6. Parmacek, M. S., and Solaro, R. J. (2004) Biology of the troponin complex in cardiac myocytes. *Prog Cardiovasc Dis* 47.
7. French, J. K., and White, H. D. (2004) Clinical implications of the new definition of myocardial infarction. *Heart* 90.
8. Antman, E. M., Tanasijevic, M. J., Thompson, B., Schactman, M., McCabe, C. H., Cannon, C. P., Fischer, G. A., Fung, A. Y., Thompson, C., Wybenga, D., and Braunwald, E. (1996) Cardiac-specific troponin I levels to predict the risk of mortality in patients with acute coronary syndromes. *N Engl J Med* 335.

9. Jacquet, S., Nishino, Y., Kumphune, S., Sicard, P., Clark, J. E., Kobayashi, K. S., Flavell, R. A., Eickhoff, J., Cotten, M., and Marber, M. S. (2008) The role of RIP2 in p38 MAPK activation in the stressed heart. *J Biol Chem* 283.
10. Lowbeer, C., Kawakami, T., Tahepjld, P., Gustafsson, S. A., Vaage, J., and Valen, G. (2002) Importance of preanalytical handling of samples for measurement of cardiac troponin T in coronary effluent from isolated rat hearts. *Scand J Clin Lab Invest* 62.
11. Clark, J. E., Kottam, A., Motterlini, R., and Marber, M. S. (2008) Measuring left ventricular function in the normal, infarcted and CORM-3-preconditioned mouse heart using complex admittance-derived pressure volume loops. *J Pharmacol Toxicol Methods*.
12. Eckle, T., Grenz, A., Kohler, D., Redel, A., Falk, M., Rolauffs, B., Osswald, H., Kehl, F., and Eltzschig, H. K. (2006) Systematic evaluation of a novel model for cardiac ischemic preconditioning in mice. *Am J Physiol Heart Circ Physiol* 291.
13. Gautel, M., Furst, D. O., Cocco, A., and Schiaffino, S. (1998) Isoform transitions of the myosin binding protein C family in developing human and mouse muscles: lack of isoform transcomplementation in cardiac muscle. *Circ Res* 82.
14. Shevchenko, A., Wilm, M., Vorm, O., and Mann, M. (1996) Mass spectrometric sequencing of proteins silver-stained polyacrylamide gels. *Anal Chem* 68.
15. Jacquet, S., Zarrinpashneh, E., Chavey, A., Ginion, A., Leclerc, I., Viollet, B., Rutter, G. A., Bertrand, L., and Marber, M. S. (2007) The relationship between p38 mitogen-activated protein kinase and AMP-activated protein kinase during myocardial ischemia. *Cardiovasc Res* 76.
16. Marber, M. S., Mestril, R., Chi, S. H., Sayen, M. R., Yellon, D. M., and Dillmann, W. H. (1995) Overexpression of the rat inducible 70-kD heat stress protein in a transgenic mouse increases the resistance of the heart to ischemic injury. *J Clin Invest* 95.
17. Van Eyk, J. E., Powers, F., Law, W., Larue, C., Hodges, R. S., and Solaro, R. J. (1998) Breakdown and release of myofilament proteins during ischemia and ischemia/reperfusion in rat hearts: identification of degradation products and effects on the pCa-force relation. *Circ Res* 82.
18. Zweier, J. L., and Talukder, M. A. (2006) The role of oxidants and free radicals in reperfusion injury. *Cardiovasc Res* 70.
19. Schroder, E., Brennan, J. P., and Eaton, P. (2008) Cardiac peroxiredoxins undergo complex modifications during cardiac oxidant stress. *Am J Physiol Heart Circ Physiol* 295.
20. Flashman, E., Redwood, C., Moolman-Smook, J., and Watkins, H. (2004) Cardiac myosin binding protein C: its role in physiology and disease. *Circ Res* 94.
21. Sadayappan, S., Osinska, H., Klevitsky, R., Lorenz, J. N., Sargent, M., Molkentin, J. D., Seidman, C. E., Seidman, J. G., and Robbins, J. (2006) Cardiac myosin binding protein C phosphorylation is cardioprotective. *Proc Natl Acad Sci USA* 103.
22. Yuan, C., Guo, Y., Ravi, R., Przyklenk, K., Shilkofski, N., Diez, R., Cole, R. N., and Murphy, A. M. (2006) Myosin binding protein C is differentially phosphorylated upon myocardial stunning in canine and rat hearts—evidence for novel phosphorylation sites. *Proteomics* 6.
23. Diamandis, E. P. (2004) Mass spectrometry as a diagnostic and a cancer biomarker discovery tool: opportunities and potential limitations. *Mol Cell Proteomics* 3.
24. Martinez-Pinna, R., Martin-Ventura, J. L., Mas, S., Blanco-Colio, L. M., Tunon, J., and Egido, J. (2008) Proteomics in atherosclerosis. *Curr Atheroscler Rep* 10.
25. Edwards, A. V., White, M. Y., and Cordwell, S. J. (2008) The role of proteomics in clinical cardiovascular biomarker discovery. *Mol Cell Proteomics* 7.
26. Mateos-Caceres, P. J., Garcia-Mendez, A., Lopez Farre, A., Macaya, C., Nunez, A., Gomez, J., Alonso-Orgaz, S., Carrasco, C., Burgos, M. E., de Andres, R., Granizo, J. J., Farre, J., and Rico, L. A. (2004) Proteomic analysis of plasma from patients during an acute coronary syndrome. *J Am Coll Cardiol* 44.
27. Koomen, J. M., Wilson, C. R., Guthrie, P., Androlewicz, M. J., Kobayashi, R., and Taegtmeyer, H. (2006) Proteome analysis of isolated perfused organ effluent as a novel model for protein biomarker discovery. *J Proteome Res* 5.
28. Srinivasan, M., Rihal, C., Holmes, D. R., and Prasad, A. (2009) Adjunctive thrombectomy and distal protection in primary percutaneous coronary intervention: impact on microvascular perfusion and outcomes. *Circulation* 119.

TABLE 1

Known biomarkers of myocardial infarction identified by 1 dimensional electrophoresis and LC-MS/MS of the coronary effluent.

| Proteins Name | Accession Number | Molecular Weight (kDa) | unique peptide in control | unique peptide in Ischemia | ratio ischemia/control |
|---|---|---|---|---|---|
| Troponin I, cardiac muscle - | TNNI3_MOUSE | 24 | 0 | 66 | +++ |
| Troponin T, cardiac muscle - | TNNT2_MOUSE | 36 | 0 | 5 | +++ |
| Troponin C, slow skeletal and cardiac muscles - | TNNC1_MOUSE | 18 | 0 | 11 | +++ |
| Creatine kinase B-type - | KCRB_MOUSE | 43 | 6 | 24 | 4.0 |
| Creatine kinase M-type - | KCRM_MOUSE | 43 | 37 | 306 | 8.3 |
| Fatty acid-binding protein, heart - | FABPH_MOUSE | 15 | 6 | 68 | 11.3 |
| L-lactate dehydrogenase A chain - | LDHA_MOUSE | 36 | 31 | 205 | 6.6 |
| L-lactate dehydrogenase B chain - | LDHB_MOUSE | 37 | 56 | 349 | 6.2 |
| Myoglobin - | MYG_MOUSE | 17 | 45 | 237 | 5.3 |
| Myosin light chain 1, skeletal muscle isoform - | MLE1_MOUSE | 21 | 0 | 4 | +++ |
| Myosin light chain 3 - | MYL3_MOUSE | 22 | 5 | 26 | 5.2 |
| Alpha-enolase - | ENOA_MOUSE | 47 | 39 | 49 | 1.3 |
| Beta-enolase - | ENOB_MOUSE | 47 | 59 | 206 | 3.5 |

The normalized spectral count was computed using Scaffold software (Proteomesoftware, v2.0) and protein release was expressed as a ratio using the control count as the denominator and ischemic count as the numerator.
"+++" indicates proteins identified in coronary effluent from ischemic but not control hearts (denominator is zero).

TABLE 2

Known biomarkers of myocardial infarction identified by 2 dimensional electrophoresis.

| Spot identification | Protein name | Accession Number | Molecular Weight (kDa) | ischemia/control fold |
|---|---|---|---|---|
| 55 | Troponin T | TNNT2_MOUSE | 35 | 4.5 |
| 187 | Troponin C | TNNC1_MOUSE | 18 | 4.23 |
| 56 | Creatine kinase B-type | KCRB_MOUSE | 42 | 4.5 |
| 69 | Creatine kinase M-type | KCRM_MOUSE | 43 | 15.3 |
| 71 | Creatine kinase M-type | KCRM_MOUSE | 43 | 15.1 |
| 83 | L-lactate dehydrogenase B chain | LDHB_MOUSE | 36 | 8.2 |
| 84 | L-lactate dehydrogenase B chain | LDHB_MOUSE | 36 | 17.9 |
| 107 | L-lactate dehydrogenase A chain | LDHA_MOUSE | 36 | 7.0 |
| 108 | L-lactate dehydrogenase A chain | LDHA_MOUSE | 36 | 4.8 |
| 138 | Myosin light polypeptide 3 | MYL3_MOUSE | 22 | 10.1 |
| 184 | Myoglobin | MYG_MOUSE | 17 | 20.7 |
| 185 | Myoglobin | MYG_MOUSE | 17 | 22.7 |
| 192 | Fatty acid-binding protein, heart | FABPH_MOUSE | 14 | 9.4 |
| 193 | Fatty acid-binding protein, heart | FABPH_MOUSE | 14 | 14.2 |
| 194 | Fatty acid-binding protein, heart | FABPH_MOUSE | 14 | 11.1 |
| 195 | Fatty acid-binding protein, heart | FABPH_MOUSE | 14 | 20.4 |

The fluorescence intensity (Cy3 and Cy5) for each spot was measured and the ratio calculated using Cy5 as numerator and Cy3 as denominator to express release after ischemia as a ratio of that with matched control perfusion.

TABLE 3

Proteins involved in the oxidative stress response that were identified in coronary effluents using the 1D-, or 2D-, based approach. The fold variation was calculated as described in Tables 1 and 2.

| | Protein Name | Accession Number | Molecular Weight (kDa) | ischemia/control fold |
|---|---|---|---|---|
| 1D gel | Aflatoxin B1 aldehyde reductase member 2 | ARK72_MOUSE | 41 | +++ |
| | Catalase - | CATA_MOUSE | 60 | 0.6 |
| | Extracellular superoxide dismutase [Cu—Zn] | SODE_MOUSE | 27 | 4.0 |
| | Glutaredoxin-3 - | GLRX3_MOUSE | 38 | +++ |
| | Glutaredoxin-3 - | GLRX3_MOUSE | 38 | +++ |
| | Glutathione peroxidase 1 - | GPX1_MOUSE | 22 | 0.7 |
| | Glutathione peroxidase 3 | GPX3_MOUSE | 25 | 1.9 |
| | Glutathione reductase, | GSHR_MOUSE | 54 | 2.3 |
| | Glutathione S-transferase A4 - | GSTA4_MOUSE | 26 | 3.6 |
| | Glutathione S-transferase Mu 1 - | GSTM1_MOUSE | 26 | 5.2 |
| | Glutathione S-transferase Mu 2 - | GSTM2_MOUSE | 26 | 5.7 |
| | Glutathione S-transferase Mu 5 - | GSTM5_MOUSE | 27 | +++ |
| | Glutathione S-transferase Mu 7 - | GSTM7_MOUSE | 26 | 2.0 |
| | Glutathione S-transferase P 1 - | GSTP1_MOUSE | 24 | 4.5 |
| | Glutathione synthetase - | GSHB_MOUSE | 52 | +++ |
| | Methionine-R-sulfoxide reductase B3 | MSRB3_MOUSE | 20 | +++ |
| | Peptide methionine sulfoxide reductase - | MSRA_MOUSE | 26 | 9.0 |
| | Peroxiredoxin-1 - | PRDX1_MOUSE | 22 | 4.3 |
| | Peroxiredoxin-2 - | PRDX2_MOUSE | 22 | 3.9 |
| | Peroxiredoxin-5 | PRDX5_MOUSE | 22 | 3.8 |
| | Peroxiredoxin-6 - | PRDX6_MOUSE | 25 | 5.0 |
| | Superoxide dismutase [Cu—Zn] - | SODC_MOUSE | 16 | 1.7 |
| | Thioredoxin - | THIO_MOUSE | 12 | 2.0 |
| | Thioredoxin domain-containing protein 17 - | TXD17_MOUSE | 14 | +++ |
| | Thioredoxin reductase 1, cytoplasmic - | TRXR1_MOUSE | 67 | +++ |
| | Xanthine dehydrogenase/oxidase | XDH_MOUSE | 147 | 1.4 |
| 2D gel | Glutaredoxin-3 - | GLRX3_MOUSE | 38 | 2.7 |
| | Hydroxyacylglutathione hydrolase - | GLO2_MOUSE | 29 | 2.4 |
| | Peroxiredoxin-1 - | PRDX1_MOUSE | 22 | 3.8 |
| | Peroxiredoxin-2 - | PRDX2_MOUSE | 22 | 8.0 |
| | Peroxiredoxin-5, mitochondrial precursor - | PRDX5_MOUSE | 22 | 20.7 |
| | Peroxiredoxin-6 - | PRDX6_MOUSE | 25 | 16.2 |
| | Peroxiredoxin-6 - | PRDX6_MOUSE | 25 | 7.5 |
| | Peroxiredoxin-6 - | PRDX6_MOUSE | 25 | 6.4 |
| | Superoxide dismutase [Cu—Zn] - | SODC_MOUSE | 16 | 8.1 |
| | Superoxide dismutase [Cu—Zn] - | SODC_MOUSE | 16 | 4.8 |
| | Thioredoxin - | THIO_MOUSE | 12 | 2.0 |

TABLE 4

Proteins released into the coronary effluent at similar abundance, and with similar ischemia selectivity, as established biomarkers Known as biomarkers appear in red text and potential candidate biomarkers in black text. A cut-off of a 5-fold enrichment in post-ischemic effluent has been used.

| Protein Identification | Protein Name | Accession Number | ischemia/ control fold | Role |
|---|---|---|---|---|
| 14 | L-lactate dehydrogenase B chain - | LDHB_MOUSE | 6.2 | Glycolysis |
| 17 | Myoglobin - | MYG_MOUSE | 5.3 | Oxygen storage/transport |
| 22 | Creatine kinase M-type - | KCRM_MOUSE | 8.3 | Energy transduction |
| 28 | L-lactate dehydrogenase A chain - | LDHA_MOUSE | 6.6 | Glycolysis |
| 31 | Malate dehydrogenase, cytoplasmic - | MDHC_MOUSE | 8.0 | Glycolysis |
| 32 | Fructose-bisphosphate aldolase A - | ALDOA_MOUSE | 5.0 | Glycolysis |
| 39 | Triosephosphate isomerase - | TPIS MOUSE | 6.3 | Glycolysis |
| 46 | Phosphoglucomutase-1 - | PGM1_MOUSE | 5.6 | Glycolysis |
| 47 | Vinculin - | VINC_MOUSE | 7.1 | Adhesion protein |
| 57 | Elongation factor 1-alpha 1 - | EF1A1_MOUSE | 5.8 | Protein biosynthesis |
| 65 | Glutathione S-transferase Mu 1 - | GSTM1_MOUSE | 5.2 | Detoxication of ROS |
| 66 | Selenium-binding protein 1 - | SBP1_MOUSE | 9.5 | Antioxidant protein |
| 71 | Adenosylhomocysteinase - | SAHH_MOUSE | 5.4 | Adenosine metabolism |
| 86 | Myosin-binding protein C, cardiac-type - | MYPC3_MOUSE | 19.3 | Thick filament associated proteins |
| 93 | Creatine kinase B-type - | KCRB_MOUSE | 4.0 | Energy transduction |
| 95 | Glutathione S-transferase Mu 2 - | GSTM2_MOUSE | 5.7 | Energy transduction |
| 96 | Heat shock-related 70 kDa protein 2 - | HSP72_MOUSE | 6.0 | Chaperone protein |
| 97 | Fatty acid-binding protein, heart - | FABPH_MOUSE | 11.3 | Transport of Fatty acid |
| 98 | Elongation factor 2 - | EF2_MOUSE | 11.7 | Protein translocation (Ribosome) |
| 111 | Myosin light chain 3 - | MYL3_MOUSE | 5.2 | filament proteins |
| 112 | Proteasome subunit beta type-5 precursor - | PSB5_MOUSE | 7.6 | Proteasome |
| 113 | WD repeat-containing protein 1 - | WDR1_MOUSE | 9.4 | Disassembly of actin filament |

The invention claimed is:

1. A method of diagnosing cardiac injury comprising identifying an elevated concentration of cardiac myosin binding protein C (cMyBP-C) or a fragment thereof or myosin regulatory light chain 2 (MLC2) or a fragment thereof in a sample obtained from a subject.

2. The method according to claim 1, wherein the cardiac injury is acute myocardial infarction or reinfarction.

3. The method according to claim 1, wherein the method comprises identifying an elevated concentration of cMyBP-C.

4. The method according to claim 1, wherein the method comprises identifying an elevated concentration of a fragment of cMyBP-C.

5. The method according to claim 4, wherein the fragment has a mass of about 4 OkDa.

6. The method according to claim 4, wherein the fragment comprises an amino acid sequence having substantial homology to the sequence of amino acids 1 to 362 of cMyBP-C.

7. The method according to claim 1, wherein the method comprises identifying an elevated concentration of MLC2.

8. The method according to claim 1, wherein the sample is a blood sample.

9. The method according to claim 8, wherein the sample is a peripheral venous sample.

10. The method according to claim 8, wherein the sample is a sample that was obtained within 24 hours of the onset of symptoms of cardiac injury.

11. A kit for diagnosing AMI, comprising at least two of the following:
- a labeled binding molecule that binds specifically to cMyBP-C;
- a labeled binding molecule that binds specifically to a fragment of cMyBP-C;
- a labeled binding molecule that binds specifically to MLC2; or
- a labeled binding molecule that binds specifically to a fragment of MLC2.

12. The kit according to claim 11, comprising a labeled binding molecule that binds specifically to cMyBP-C and a labeled binding molecule that binds specifically to a fragment of cMyBP-C.

* * * * *

UNITED STATES PATENT AND TRADEMARK OFFICE
CERTIFICATE OF CORRECTION

| | | |
|---|---|---|
| PATENT NO. | : 8,546,089 B2 | Page 1 of 1 |
| APPLICATION NO. | : 13/319484 | |
| DATED | : October 1, 2013 | |
| INVENTOR(S) | : Manuel Mayr et al. | |

It is certified that error appears in the above-identified patent and that said Letters Patent is hereby corrected as shown below:

In the Specification:

In Column 2, Line 57, Change "uniprot)" to --uniprot/)--.

In Column 3, Line 62, Change "immunobloting." to --immunoblotting.--.

In Column 4, Line 48, Change "immunobloting" to --immunoblotting--.

In Column 5, Line 6, Change "acetonitril" to --acetonitrile--.

In Column 7, Line 64, Change "Bromphenol" to --Bromophenol--.

In Column 9, Line 19, Change "Zobrax" to --Zorbax--.

In Column 10, Line 27, Change "immunobloting" to --immunoblotting--.

In the Claims:

In Column 17, Line 45, In Claim 5, change "4 OkDa." to --40 kDa.--.

Signed and Sealed this
Twenty-ninth Day of July, 2014

Michelle K. Lee
*Deputy Director of the United States Patent and Trademark Office*